(12) United States Patent
Van Bruggen et al.

(10) Patent No.: US 10,849,594 B2
(45) Date of Patent: Dec. 1, 2020

(54) CATHETER DEVICE

(71) Applicant: KONINKLIJKE PHILIPS N.V., Eindhoven (NL)

(72) Inventors: Michel Paul Barbara Van Bruggen, Helmond (NL); Pippinus Maarten Robertas Wortelboer, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 281 days.

(21) Appl. No.: 15/735,844

(22) PCT Filed: Jun. 6, 2016

(86) PCT No.: PCT/EP2016/062751
§ 371 (c)(1),
(2) Date: Dec. 12, 2017

(87) PCT Pub. No.: WO2016/202618
PCT Pub. Date: Dec. 22, 2016

(65) Prior Publication Data
US 2018/0168540 A1    Jun. 21, 2018

(30) Foreign Application Priority Data
Jun. 19, 2015   (EP) .................................... 15172939

(51) Int. Cl.
*A61B 8/12*          (2006.01)
*A61B 8/00*          (2006.01)
(Continued)

(52) U.S. Cl.
CPC .............. *A61B 8/12* (2013.01); *A61B 5/0826* (2013.01); *A61B 8/445* (2013.01); *A61B 8/4488* (2013.01);
(Continued)

(58) Field of Classification Search
None
See application file for complete search history.

(56) References Cited

U.S. PATENT DOCUMENTS 4,326,416 A     4/1982  Fredberg
5,331,967 A *   7/1994  Akerson ............... A61M 16/04
                                                    128/207.14
(Continued)

FOREIGN PATENT DOCUMENTS

CN      102008283 B      5/2012
EP      1447048 A1       8/2004
(Continued)

OTHER PUBLICATIONS

Hoffstein, V. et al., "The acoustic reflection technique for non-invasive assessment of upper airway area", European Respiratory Journal, 4.5, 1991, pp. 602-611.
(Continued)

*Primary Examiner* — Etsub D Berhanu
*Assistant Examiner* — Aurelie H Tu (57) ABSTRACT

The invention provides a catheter (12) comprising longitudinally spaced acoustic emitters (S1, S2) and receivers (M1, M2, M3) for use in determining the locations of obstructions in an upper airway of a patient. A plurality of emitters and plurality of receivers are provided, such that, when inserted into an upper airway or oral cavity, the relative attenuation of signals received at each receiver from each emitter may be used to determine the existence and/or extent of obstructions located along the propagation path between each of the various emitter-receiver pairs. Also provided are methods for determining the locations of obstructions in an upper airway using signals received from acoustic receivers as comprised by catheter arrangements according to embodiments of the invention.

10 Claims, 2 Drawing Sheets

(51) Int. Cl.
    *A61M 16/04* (2006.01)
    *A61B 5/08* (2006.01)
    *A61B 8/08* (2006.01)
(52) U.S. Cl.
    CPC ....... *A61B 8/5223* (2013.01); *A61M 16/0461* (2013.01); *A61M 2205/3375* (2013.01)

(56) References Cited

U.S. PATENT DOCUMENTS

| | | |
|---|---|---|
| 5,810,741 A | 9/1998 | Essen-Moller |
| 6,038,468 A * | 3/2000 | Rex .................. A61B 5/06 600/424 |
| 6,761,693 B1 | 7/2004 | Rasmussen |
| 2011/0160584 A1* | 6/2011 | Paul .................. A61B 8/0883 600/439 |
| 2012/0123286 A1 | 5/2012 | Wilson |
| 2014/0330151 A1 | 11/2014 | Wilson |

FOREIGN PATENT DOCUMENTS

| | | |
|---|---|---|
| GB | 2326709 A | 12/1998 |
| WO | 2001032082 A1 | 5/2001 |
| WO | 2001091843 A1 | 12/2001 |
| WO | 2007144626 A1 | 12/2007 |
| WO | 2015162140 A1 | 10/2015 |

OTHER PUBLICATIONS

Fujimoto, Y. et al., "A three-microphone acoustic reflection technique using transmitted acoustic waves in the airway", Journal of Applied Physiology, 115: 1119-1125, 2013.

* cited by examiner

CATHETER DEVICE

CROSS-REFERENCE TO PRIOR APPLICATIONS

This application is the U.S. National Phase application under 35 U.S.C. § 371 of International Application Serial No. PCT/EP2016/062751, filed on Jun. 6, 2016, which claims the benefit of European Application No. 15172939.9, filed on Jun. 19, 2015. These applications are hereby incorporated by reference herein.

FIELD OF THE INVENTION

The invention relates to a catheter device and related methods for determining locations of obstructions in an upper airway.

BACKGROUND OF THE INVENTION

Obstructive sleep apnea (OSA) is the most common kind of sleep apnea, affecting up to one in eighteen people, and is characterized by the occurrence of pauses in breathing, or instances of shallow or infrequent breathing, during sleep. It is caused by blockage or obstruction of the oral cavity or upper airway, often due to loss of muscular tone induced by the onset of old age, or by abuse of drugs or alcohol.

A range of therapies exist for treatment of OSA, the most common of which is positive airway pressure (PAP), in which a ventilator is used to deliver a controlled stream of air through the airway, in order to hold open lax muscles which are obstructing breathing. PAP is particularly appropriate in more severe cases, where patients exhibit an apnea hypopnea index (AHI)>30. In more mild and moderate cases (i.e. 5<AHI<30) OSA patients may also suffer from daytime sleepiness and require therapy to prevent the development of comorbidities over the longer term. Mild-moderate OSA patients often have more difficulty complying with PAP therapy because the disease burden is not as strong as in severe patients, and are therefore reluctant to submit to so invasive a therapy. In these cases, various alternative treatments exist, such as mandibular advancement, upper airway surgery and implantable devices.

In each of these therapies, however, it is important to understand which part(s) of the upper airway in particular is (are) causing obstruction, such that the therapy can be directed most effectively. One common approach is to perform an examination of the airway non-invasively using acoustic reflectometry techniques. In such techniques, acoustic waves are propagated along the airway of the patient, by an emitter, via the mouth or nose, and reflections are listened for using a microphone adjacent to the emitter. It is possible, through algorithmic analysis of the detected reflections (see for example: Hoffstein, V., and J. J. Fredberg. "The acoustic reflection technique for non-invasive assessment of upper airway area." *European Respiratory Journal* 4.5 (1991): 602-611.), to determine an estimate of the cross-sectional area of the examined airway as a function of distance from the emitter. From this, narrowing of the airway at particular locations can be identified, and the specific positions therefore of airway obstructions ascertained.

Reflectometry techniques however suffer the disadvantage that the accuracy of cross-sectional area estimations declines with distance from the emitter. This is compounded by acoustic leakage and also patient movements during the measurement process, which both act to further compromise the accuracy of the obtained results. Furthermore, since the first obstruction encountered by a wave propagating along the airway causes reflection of much of the wave's initial intensity, reflections from subsequent portions of the airway are typically too weak in intensity to derive any accurate measurements. Hence it is typically only possible to accurately determine the location of the upper-most airway obstruction using these techniques.

Desired therefore is a simple, reliable and cost-effective means by which the particular locations of all anatomical contributors to upper airway collapse in a patient may be ascertained.

SUMMARY OF THE INVENTION

The invention is defined by the claims.

According to an aspect of the invention, there is provided a catheter for use in determining the presence and location of obstructions in an upper airway, the catheter comprising:

a plurality of acoustic transducer elements positioned at different points along a length section of the catheter so as to coincide with different points along the length of said upper airway upon insertion therein, each element adapted to emit an acoustic signal; and a plurality of acoustic sensor elements positioned at different points along said length section of the catheter, each adapted to detect one or more of said acoustic signals.

The acoustic transducer elements and/or acoustic sensor elements are arranged for example such that, upon insertion of the catheter in an upper airway, the spaces between them coincide with one or more of: the velum, the oropharynx, the tongue and the epiglottis. For example, the sensor elements and the transducer elements may be interleaved, such that each sensor element is neighbored on one or both sides by a transducer element and vice versa. In this case, the interleaved sensors and transducers may be arranged such that the spaces between neighboring sensors and transducers, when inserted into the airway coincide with one of the velum, the oropharynx, the tongue and the epiglottis.

The catheter comprises a plurality of acoustic transmitters and a plurality of microphones or acoustic receivers, the transmitters and receivers mounted along, or otherwise comprised within or on, the length of the catheter. The emitters, or transducer elements, may be spaced on the catheter longitudinally with respect to one another and the acoustic receivers or detectors may be spaced on the catheter longitudinally with respect to one another. Each acoustic sensor and each acoustic transducer element may hence be separated from a neighboring sensor and/or transducer element by a longitudinal stretch of the catheter.

The plural arrangement of acoustic transmitters and receivers spaced along the catheter allows for a novel means of surveying collapse in the upper airway by measurement of direct path intensities between the plurality of emitters and the plurality of sensors, rather than by relying on acoustic reflections received at just one localized point at one end of the airway. Once inserted into the airway of a patient, any obstruction located between an emitting transducer and a receiving sensor of the catheter will attenuate the passage of the acoustic signal from the transducer to the sensor. If the locations of each of the transducers and sensors within the air passage are known, analysis of relative signal attenuations between specific emitters and specific receivers allows for a determination of the particular location of an obstruction.

In examples, the base of the tongue more specifically may be the region of interest, with the sensor elements and/or acoustic elements correspondingly arranged to coincide the velum, the oropharynx, the tongue base and the epiglottis.

These four are particular anatomical features of the oral cavity and upper airway at which collapse is known to occur. By spacing emitters and microphones around these features, attenuation in signal transmission caused by obstructions at these locations can be identified. In this particular example, or in other examples, the catheter may comprise three acoustic transducer elements separated by two acoustic sensor elements, and these may be spaced with respect to one another such that the four anatomical features described above coincide with the spaces between neighboring elements. These features are named by way of example only, and in other embodiments, different points of interest along the airway might instead be chosen for coincidence with transducer and/or sensor element spaces.

In some embodiments, each respective transducer element may be adapted or controlled to emit an acoustic signal of a different frequency, or different acoustic pattern. In this way each sensor element may be adapted to receive signals from each of the emitting transducer elements, and these signals may be distinguished or separated from one another in terms of their characteristic frequency or pattern and thereby identified with a particular source emitter. Signal strength from each emitter may hence be assessed at each receiver location and locations of intermediary attenuating blockages more accurately assessed.

According to a further aspect of the invention, there is provided a system for detecting and determining the location of obstructions within an upper airway, the system comprising:

a catheter as defined above; and a processing unit adapted to receive one or more outputs generated by each of the acoustic sensor elements, the outputs representative of intensities of each of the acoustic signals detected by respective sensor elements, and to determine on the basis of said intensities of detected signals the presence of any obstruction within the airway and a position of said obstruction, relative to the position of one or more of said sensor elements.

For example in some embodiments, the processing unit may be adapted to determine the presence and position of an obstruction by comparison of the signal intensities detected at each sensor element with one or more reference intensities stored in a memory. In this case, determination of an obstruction between a given sensor-emitter pair is performed by comparison of the measured signal intensity at the sensor with one or more stored intensity values, known to correspond with particular degrees of attenuation, and hence particular extents of airway blockage. For example, a different set of reference values might be consulted in the case of each different sensor-emitter pair, the values calibrated to take account of the differing distances between the pairs and/or various anatomical peculiarities of the airway regions separating them. The reference values might for example be derived empirically, by experimentation with differently sized simulated blockages, or by analytical calculation through application of an algorithm or physical model, for example.

Each sensor element may be adapted to detect the respective acoustic signals emitted by each transducer element, to thereby generate an output representative of a set of detected signals, and wherein the processing unit is adapted to determine the presence and position of an obstruction by comparison of the set of signal intensities detected at each sensor element with one or more reference sets stored in a memory. Hence analysis of individual sensor-emitter pairs might be replaced by analysis of signal sets at each sensor, these sets being compared with one or more reference sets, the reference sets known to correspond with various 'states' of the airway system as a whole, e.g. "velum blocked, everything else clear".

According to a further aspect of the invention, there is provided a processing method for determining the location of one or more obstructions in an upper airway, the method comprising:

receiving intensity values corresponding to intensities of one or more acoustic signals using acoustic sensor elements, the signals received at a plurality of detection points located along a length section of an upper airway, each detected signal deriving from an acoustic signal emitted at one of a plurality of emission points spaced along said length section of an upper airway using acoustic transducer elements, wherein the signals generated received by the acoustic transducer elements and/or the signals received by the acoustic sensor elements are generated and received at locations such that the spaces between them coincide with one or more of: the velum, the oropharynx, the tongue and the epiglottis; and determining on the basis of the detected intensities at each of the plurality of detection points, the presence and position of any obstruction within the airway, relative to the position of the detection points.

It is not necessary that such a method be performed at the time of examination of a patient with the above described catheter arrangement. Rather, the device and associated system are such that data may be collected 'blindly' (i.e. without the need for any 'live' results from the sensors at the time of recording the sensor outputs), and the gathered sensor output data subsequently analyzed by embodiments of the above processing method to determine the locations of any obstructions within the airway.

The presence and position of an obstruction may be determined through comparing the detected intensities at each of the plurality of detection points with one or more reference intensities. In particular, each detection point may receive a plurality of signals, each of said plurality deriving from one of the plurality of emission points. The determining step may then comprise grouping the totality of received signal intensities according to the detection point at which the corresponding acoustic signal was received, and comparing the hence formed groups of signal intensities against one or more reference groups stored in a memory. Each detection point might be considered individually, the intensity values corresponding to each emitted signal being used to assess a state of the airway system. Alternatively, the whole ensemble of groups of signal intensities might be considered, this ensemble being compared to one or more reference ensembles in order to assess an overall state of the airway system in terms of the locations and, in some cases, relative extent of obstructions or blockages.

Each of the acoustic signals emitted at each of the one or more emission points may have a different frequency. The determination step may comprise distinguishing between the plurality of received signals at each detection point by way of frequency analysis, and hence ascribing each to a corresponding emission point.

The emission points may interleave with the detection points and the emission points and/or detection points may be arranged such that the spaces between said points coincide with one or more of the velum, the oropharynx, the tongue and the epiglottis. In this way, the relative signal intensities at each detection point of each emitted acoustic signal may be used to identify the particular location of any attenuating blockages in the airway.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a catheter comprising longitudinally spaced acoustic emitters and receivers for use in determining the locations of obstructions in an upper airway of a patient. A plurality of emitters and plurality of receivers are provided, such that, when inserted into an upper airway, the relative attenuation of signals received at each receiver from each emitter may be used to determine the existence and/or extent of obstructions located along the propagation path between each of the various emitter-receiver pairs. Also provided are methods for determining the locations of obstructions in an upper airway using signals received from acoustic receivers as comprised by catheter arrangements according to embodiments of the invention.

Embodiments of the invention allow for more accurate determination of the location and extent of obstructions in a patient's airway, compared with more typical acoustic reflectometry techniques, as well as allowing for identification of all anatomical contributors to upper airway collapse in a patient, rather than only those closest to the top of a patient's airway (as in reflectometry). Embodiments achieve this through disposing, by means of insertion of the catheter into the airway, acoustic emitters (speakers) and receivers (microphones) at a plurality of longitudinally separated points along a patient's airway. The microphones and speakers may be arranged for example such that the spaces separating neighboring units coincide with particular anatomical areas of interest (i.e. areas of likely collapse) along the length of the airway. In this way, obstructions in the cavity may be identified directly through attenuation in signals received at particular microphones, from particular emitters. Any such attenuation indicates the existence of an obstruction positioned along the propagation path between the particular emitter and particular receiver concerned. Unlike in acoustic reflectometry techniques, wherein reflections from single or multiple acoustic signals (sent from an upper point in the airway) from airway walls is used to estimate airway cross-section, in embodiments of the present invention, attenuation of direct (or near direct) path intensities between various pairs of longitudinally disposed emitters and receivers is used to identify blockages along said paths.

Figure 1:
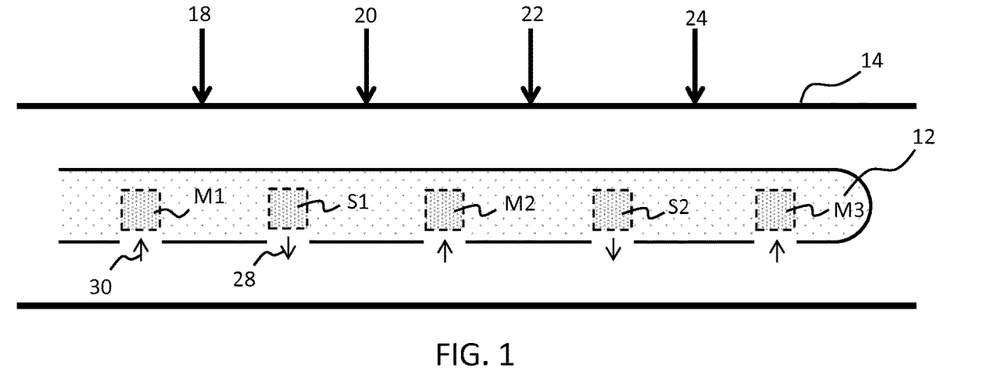
FIG. 1 shows a schematic illustration of a length section of an example catheter disposed inside an airway.

By way of illustration, FIG. 1 schematically depicts an example catheter 12 according to one or more embodiments of the invention, arranged within a stretch of an upper airway 14. Along the length of the airway are indicated four anatomical regions or features, labeled 18, 20, 22, and 24, these, by way of non-limiting example, representing the velum, the oropharynx, the tongue base and the epiglottis respectively. Disposed within the airway 14 is a catheter 12, which comprises two acoustic transducer (or speaker) elements, S1, S2 and three acoustic receiver (or microphone) elements M1, M2, M3, arranged alternately along the longitudinal extent of the catheter. In the schematic illustration of FIG. 1, speaker and microphone elements are shown embedded within the catheter 12, and the catheter is shown comprising windows or openings beneath each speaker and microphone element, allowing outgoing 28 and incoming 30 acoustic signals to be sent and received by the elements. However, in alternative examples, such windows or openings may not be necessary or desired. For example the emitters and receivers could be disposed on an outside surface of the catheter, so that openings through the catheter itself are not required.

The microphones and speakers are arranged such that the spaces between each pair of neighboring elements coincides with one of the four anatomical regions 18, 20, 22, 24. Hence, in the case of an obstruction in the region 18, for example, a signal 28 sent by speaker S1 would be attenuated by said obstruction on its path to microphone M1, and this attenuation could be detected by analysis of received signal 30, and used to hence identify the presence of the obstruction. By comparing the source intensity of the wave and the received intensity at the microphone, an extent of attenuation might also be determined and this used to estimate or assess the size or extent of the obstruction.

Figure 2:
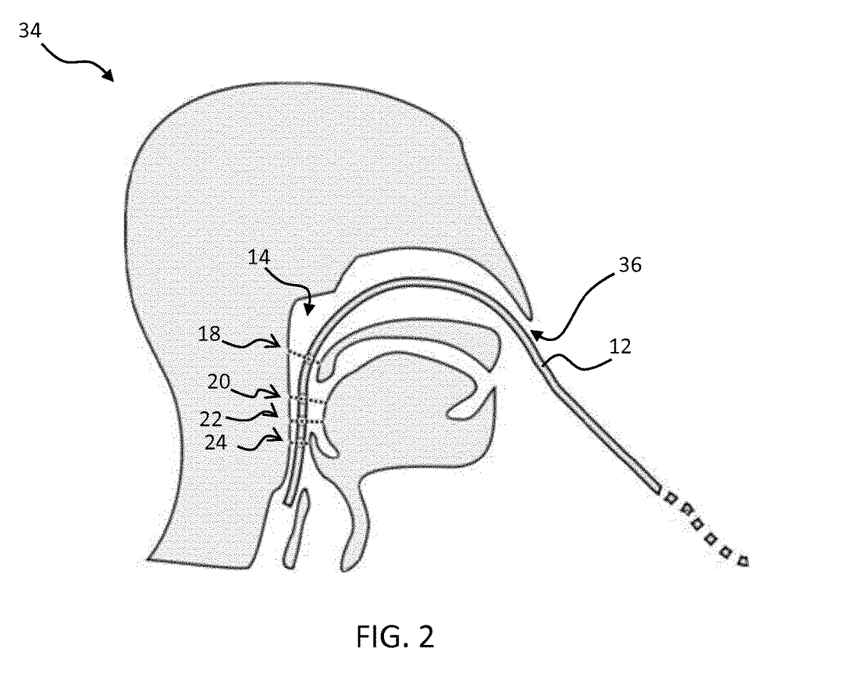
FIG. 2 shows a schematic illustration of an example catheter inserted into a patient's nasal cavity and upper airway.

For illustration, FIG. 2 schematically shows the catheter 12 disposed in the upper airway of a patient 34, having been inserted via the nose 36 of the patient. The approximate positions of the four anatomical regions of FIG. 1 (velum 18, oropharynx 20, tongue base 22, and epiglottis 24) are indicated along the airway 14 of the patient 34.

Each of the microphones M1, M2, M3 may be adapted to receive signals from each of emitters S1, S2. Hence the example obstruction at region 18 would be identifiable, not only through the attenuation of the signal sent by S1 (received at M1) but also by the equivalent attenuation of the signal sent by S2 (received at M1). A detection of equivalent attenuation in both signals may provide corroboration of the presence and extent of the obstruction, improving the reliability of results obtained using the catheter. Note that since S1 and S2 are located at differing distances from microphone M1, these differing path lengths would need to be taken into account when assessing an extent of attenuation of received signals. The signal received from S2 will naturally have a lesser intensity at M1 than signals received from the closer S1, and hence any analysis would need to be calibrated accordingly.

Each of the speakers comprised by the catheter (in the example of FIG. 1, just S1 and S2) may be adapted to generate an acoustic signal of a differing frequency. This provides a simple and convenient means for distinguishing between the multiple signals received at any given microphone element and for identifying the signals in terms of a source emitter. The capacity to identify the source emitter of the received signal may be useful for subsequent analysis of the collected data. For example, an obstruction at location 22 could be identified through determining that the signal received at microphone M2 from speaker element S2 is attenuated, while the signal received at the same microphone from S1 is not attenuated.

Obstructions might also occur for example exactly at a sensor or speaker location (rather than at a point some way between the two). This state too may be determined by analysis of signals received around the location of the blockage. If none of the sensors receives signals from speaker S1 for instance, it may be concluded that the area around S1 is completely blocking the speaker. Alternatively, if none of the signals is reaching M1, it follows that the area around M1 may be completely blocked.

According to certain examples, each of the speaker elements comprised by the catheter 12 may be adapted or controlled to generate signals of a different acoustic pattern, for example a pattern comprising a non-continuous emission or a continuous emission with a non-uniform acoustic frequency. One or more speaker elements may be adapted to emit acoustic pulses rather than continuous waves, for instance. Different speaker elements might be adapted or controlled to emit pulses at different pulse frequencies. One or more speaker elements may be adapted to generate signals which vary in frequency over time, for example oscillating continuously between an upper frequency and a lower frequency, or switching intermittently (discretely) between a first and second frequency.

Although in the particular example of FIG. 1 (and FIG. 2) the catheter 12 is shown comprising three microphone elements and two speaker elements, in other examples the catheter may comprise different numbers of each of these elements. Additional microphone and/or speaker elements may extend the longitudinal range of the sensitive region of the catheter, allowing for additional anatomical regions to be examined, for example. Alternatively, additional speaker and microphone elements may be provided along the same length stretch of the catheter, for example by narrowing the longitudinal spacing between each element. Since the particular location of any obstruction may only be known to within an accuracy equal to the width of the inter-element space within which is it positioned, a narrower spacing between elements allows for an improvement in the 'resolution' of the device: allowing more precise determination of the location of an obstruction within a patient's airway.

According to one or more examples, the single speaker and microphone elements shown in FIG. 1 might be replaced instead with one or more arrays of speaker and/or microphone elements. Depending on the shape of the array, this may for example allow for more sophisticated structural analysis of the size and/or shape of obstructions detected in the airway for example.

Although in the example of FIG. 1, microphone and speaker elements are uniformly interleaved with one another, in other examples, microphone and speaker elements might be arranged according to a different pattern. For example pairs of speaker elements might be separated by single microphone elements, or vice versa. In some cases, particular longitudinal regions of the catheter 12 might be provided with greater densities of either microphone or speaker elements, while remaining portions of the catheter follow the same alternating pattern as in FIG. 1. Microphone and/or speaker elements may be disposed on/in the catheter 12 having sensitive areas of said elements facing in different directions. For example, the linear arrangement of FIG. 1 may adapted so as to follow a spiral or helical pattern, circulating around the periphery of the catheter body.

Alternatively, speaker elements may be provided which are each adapted to emit acoustic signals in more than one propagation direction simultaneously, for example to emit omnidirectional (panoramic) acoustic waves (via an emitting ring elements for instance).

In some cases, the microphone and/or speaker elements may be provided with certain wave-directing and/or shaping elements. For example, in the case that speaker elements are arranged about the catheter such that sensitive regions face radially outwards, it may be advantageous to provide to said elements components for redirecting outgoing waves in a longitudinal direction, rather than in a radial direction. In this way, fewer reflections (in the case of neighboring elements, possibly zero reflections) are required in propagation of an emitted wave from a given speaker element to a given microphone element. Such features are not essential however, since the reflection of emitted waves from the walls of the airway 14 en-route to the various microphone elements need not impede the efficacy of the device or the accuracy of the results obtained. Reflections from airway walls will typically cause only very moderate attenuation, of an order significantly less than the attenuation which may be caused by an obstruction within the airway. Hence, obstruction-induced attenuation is likely always to be clearly distinguishable from reflection-induced attenuation.

The speaker elements may comprise for example acoustic transducer elements. These may include for instance electrodynamical loudspeakers, as used in for example in mobile devices such as smartphones or tablet computers. In alternative examples, they may include balanced-armature loudspeakers, as used in hearing-aids, for example (these are known as 'receivers' within the hearing aid field).

The microphone elements may comprise for example MEMS microphones, as for example used in cell-phones, or electret microphones as used in hearing aids.

According to aspects of the invention, there is provided a system and a method for determining, by processing or analysis of data obtained using one or more embodiments of the above described catheter, the location of one or more obstructions in a patient's upper airway and/or oral cavity. By way of illustration, a particular (non-limiting) example of such a method will now be described in detail with reference to the example catheter 12 shown in FIG. 1 and described above. It should be noted that this method, and any other example methods in accordance with the invention, are methods of processing and analysis and need not be performed at the same time as data is collected from a patient using embodiments of the catheter.

On insertion of the catheter 12 into a patient's upper airway (for example as illustrated in FIG. 2) and alignment of the spaces between neighboring microphone and speaker elements with the four anatomical regions (abbreviated hereafter by) V (the velum 18), O (the oropharynx 20), T (the tongue base 22), and E (the epiglottis 24) shown, acoustic signals are emitted from each of the speaker elements S1 and S2, having acoustic frequency F1 and F2 respectively.

At each of the three microphone elements M1, M2, M3, signals are received from each of the two speaker elements S1, S2. These signals may be distinguished and hence identified with one of the two speaker elements by means of their differing frequencies F1 and F2. The various signals which are received across the different microphone elements, from the various speaker elements, may be understood by means of a transfer function, represented by the notation $T_{\alpha\beta}$, wherein $\alpha$ denotes the microphone at which the signal T is received, and $\beta$ denotes the speaker from which the signal was sent. The transfer function $T_{\alpha\beta}$ represents the degree or extent to which a signal emitted by the speaker element $\beta$ is received at the microphone element $\alpha$. It represents an absolute measure of the strength or intensity of the signal as detected and observed at microphone $\alpha$. By comparison of this measure with known maximum and minimum baseline levels of the signal, the transfer function $T_{\alpha\beta}$ may be used to determine a degree of attenuation of the signal which has been received at microphone $\alpha$. The attenuation level of the signal may then be used to estimate a collapse extent of one or more sections of the upper airway.

In order to derive an attenuation level of the signal $T_{\alpha\beta}$, an attenuation function may be employed, which depends upon one or more known baseline levels of the signal. The baseline levels might typically correspond to known or expected intensity levels of the signal for certain defined maximal or minimal obstruction states of the airway.

According to one example, for instance, the attenuation function might take the following form:

$$\gamma(T_{\alpha\beta}, T_{\alpha\beta O}, T_{\alpha\beta C}) = \frac{T_{\alpha\beta O} - T_{\alpha\beta}}{T_{\alpha\beta O} - T_{\alpha\beta C}}$$

where $T_{\alpha\beta O}$ represents the expected intensity level of a signal received at microphone α from speaker β when there is no obstruction between microphone and speaker ('Open' baseline), and $T_{\alpha\beta C}$ represents the expected intensity level of a signal received at microphone α from speaker β when there is complete obstruction between microphone and speaker ('Closed baseline').

The value of the function γ gives a proportional measure, between 0 and 1, of the degree to which the level of signal $T_{\alpha\beta}$ matches the Closed baseline level $T_{\alpha\beta O}$, i.e. gives a proportional measure of the level of attenuation, where γ=1 would show an attenuation level commensurate with complete airway blockage ($T_{\alpha\beta}=T_{\alpha\beta C}$), and γ=0 would show an attenuation level commensurate with zero airway blockage ($T_{\alpha\beta}=T_{\alpha\beta O}$).

For example, referring to FIG. 1, in the case that the airway 14 is completely open (i.e. no collapse at any of points V,O,T,E), then the signal received at M1, from S1 ($T_{11}$) and S2 ($T_{12}$) respectively, would correspond to the Open baseline values $T_{11}=T_{11O}$ and $T_{12}=T_{12O}$. The attenuation functions in these cases would then give the following values $$\gamma(T_{11}, T_{11O}, T_{11C}) = \frac{T_{11O} - T_{11O}}{T_{11O} - T_{11C}} = 0$$

and $$\gamma(T_{12}, T_{12O}, T_{12C}) = \frac{T_{12O} - T_{12O}}{T_{12O} - T_{12C}} = 0$$

These are the attenuation function results for (relative) zero attenuation signals of frequency F1 and F2 respectively (i.e. the Open baseline levels of speakers S1 and S2 at M1); In this Open case, the measured intensity of each relates principally to the path length between M1 and S1 and M1 and S2 respectively.

To take a second example, in the case that there is complete blockage at the location of the oropharynx only, then the signals received at M1 from S1($T_{11}$) and S2 ($T_{12}$) respectively would correspond to the baseline levels $T_{11}=T_{11O}$ and $T_{12}=T_{12C}$. The blockage at O would attenuate the signal from S2 since it lies along the propagation path between S2 and M1. Hence M1 would register the Closed baseline attenuated signal $T_{12C}$ from speaker S2. However, the blockage does not attenuate the signal from speaker S1, hence M1 would register the Open baseline signal $T_{11O}$ from S1. The attenuation functions in this case would be given by:

$$\gamma(T_{11}, T_{11O}, T_{11C}) = \frac{T_{11O} - T_{11O}}{T_{11O} - T_{11C}} = 0$$

and $$\gamma(T_{12}, T_{12O}, T_{12C}) = \frac{T_{12O} - T_{12C}}{T_{12O} - T_{12C}} = 1$$

corresponding to a baseline 'Closed' blockage state between M1 and S2, but a baseline 'Open' blockage state between M1 and S1.

Note that if the signals employed by the device have frequencies which are too higher, for example having a wavelength of a similar dimension to the distance between the microphones, destructive interference may occur. This may in turn result in false positives in certain cases. According to certain examples therefore, the signal frequencies may be limited to a range of wavelengths of magnitude preferably smaller than one third of the distance between the two outer transducers.

In the vast majority of real-world cases, the attenuation function γ would not result in either of the extreme values 0 or 1, but rather would provide some fractional value between the two, corresponding to some degree of partial blockage or obstruction between respective microphone and speaker pairs, α, β. For example, referring again to FIG. 1, in the case that there were partial obstruction at the position of the oropharynx, of an extent covering roughly half the total size of the airway cross-section, the transfer function of the signal received at microphone M1 from speaker S2 may typically correspond to a value equal approximately to $T_{12}=T_{12C}/2$, i.e. a received signal intensity of a magnitude half of that of the Closed baseline level. In this case, the attenuation function for $T_{12}$ would give the value:

$$\gamma(T_{12}, T_{12O}, T_{12C}) = \frac{T_{12O} - \frac{T_{12C}}{2}}{T_{12O} - T_{12C}} = \frac{1}{2}$$

Similar attenuation functions may be derived for determining or estimating an extent of collapse at each of the anatomical regions under examination. In the present example, attenuation levels at each of the velum, oropharynx, tongue (base) and epiglottis respectively may be determined through evaluating the following:

$$\text{Collapse Extent at Velum} = \gamma(T_{11}, T_{11O}, T_{11C}) = \frac{T_{11O} - T_{11}}{T_{11O} - T_{11C}}$$

$$\text{Collapse Extent at Oropharynx} = \gamma(T_{21}, T_{21O}, T_{21C}) = \frac{T_{21O} - T_{21}}{T_{21O} - T_{21C}}$$

$$\text{Collapse Extent at Tongue} = \gamma(T_{22}, T_{22O}, T_{22C}) = \frac{T_{22O} - T_{22}}{T_{22O} - T_{22C}}$$

$$\text{Collapse Extent at Epiglottis} = \gamma(T_{32}, T_{32O}, T_{32C}) = \frac{T_{32O} - T_{32}}{T_{32O} - T_{32C}}$$

The set of baseline levels $T_{\alpha\beta O}$ and $T_{\alpha\beta C}$ provide a convenient means not only of determining or estimating a collapse state at a particular single anatomical location, but also of determining more comprehensively an overall collapse state of the airway, across the whole set of anatomical locations under examination. As with collapse states for individual locations, overall collapse states can be estimated by comparison with known overall (or 'global') baseline states, each global baseline state describing a ordered set of local baseline states of either absolute collapse or zero collapse at each of the anatomical regions. Each global baseline state may be associated its own unique pattern or set of local baseline signals which may be expected to be received across each of the microphone elements, in the case that the baseline state is realized.

The global baseline collapse states may be conveniently codified in terms of the already described set of local baselines signal values $T_{\alpha\beta O}$ and $T_{\alpha\beta C}$. Table 1 (below) lists an illustrative sample of possible baseline collapse states of the airway system and the corresponding signals which are received as a consequence at each of the microphones M1, M2 and M3. The collapse states are each denoted by the notation (V, O, T, E) where V, O, T, and E refer to the anatomical regions 18, 20, 22, 24 along the airway in FIG. 1, and each take a value of 1 to denote a blockage at that location, or a value of 0 to denote no blockage. These collapse states correspond to absolute or baseline collapse states: states in which collapse at each of V, O, T, E is either at a baseline Open level, or a baseline Closed level.

TABLE 1

| Collapse pattern (VOTE) | Signal M1 | Signal M2 | Signal M3 |
|---|---|---|---|
| (0, 0, 0, 0) | ($S_{1, 1, O}$; $S_{1, 2, O}$) | ($S_{2, 1, O}$; $S_{2, 2, O}$) | ($S_{3, 1, O}$; $S_{3, 2, O}$) |
| (1, 0, 0, 0) | ($S_{1, 1, C}$; $S_{1, 2, C}$) | ($S_{2, 1, O}$; $S_{2, 2, O}$) | ($S_{3, 1, O}$; $S_{3, 2, O}$) |
| (0, 0, 0, 1) | ($S_{1, 1, O}$; $S_{1, 2, O}$) | ($S_{2, 1, O}$; $S_{1, 2, O}$) | ($S_{3, 1, C}$; $S_{3, 2, C}$) |
| (1, 0, 1, 0) | ($S_{1, 1, C}$; $S_{1, 2, C}$) | ($S_{2, 1, O}$; $S_{1, 2, C}$) | ($S_{3, 1, C}$; $S_{3, 2, O}$) |
| (1, 1, 1, 1) | ($S_{1, 1, C}$; $S_{1, 2, C}$) | ($S_{2, 1, C}$; $S_{2, 2, C}$) | ($S_{3, 1, C}$; $S_{3, 2, C}$) |
| ... | ... | ... | ... |

Note that M1 can also receive a signal from S2 at the other end; this provides a second means to detect restrictions, but it is less specific: it only detects the maximum restriction in the path along 18 (V) 20 (O) and 22 (T).

It will be understood that, given the fixed positions of the two speaker elements, only a finite number of particular distinct baseline signal traces may ever be received at the three microphone elements, depending upon the particular baseline collapse state of the airway system. Furthermore, for each of the possible baseline collapse states (V,O,T,E), a unique set of three signal pairs (i.e. a unique row, as shown in Table 1) are received by the three microphones respectively. By forming an 'audio-catalogue', for example, of the individual baseline signals listed in (an exhaustive version of) Table 1, and using this catalogue as a reference for comparison with received signals, each signal $T_{\alpha\beta}$ received at each microphone may be uniquely identified in terms of a particular baseline value. Once all signals being received across the microphones at a given moment have been identified in this manner, the particular set of three pairs of signals being detected may be compared with rows of Table 1, and in this way a corresponding overall collapse state of the airway uniquely identified.

Of course, as with local collapse states, in real-world cases, the global collapse state of the airway system will almost never match exactly with any of the known baseline states, but rather will correspond only to some fractional extent. Hence, an overall 'extent of collapse' of the airway system may in embodiments be sought, wherein a likely collapse state of the whole (V,O,T,E) system is determined through considering the extent of correspondence between an actual detected set of three pairs of signals and the various reference sets of signals in (an exhaustive version of) Table 1 (or a similar such table).

This might be done, for example, by determining individually (as in the above described procedure for localized states) a collapse extent percentage for each of V,O,T,E along the airway and then collating this information together to form a picture of the likely state of the whole airway system. Alternatively, however, each received signal at each microphone might be compared with each of the four possible reference signals for a given microphone, and a correspondence extent worked out for each. Based on the highest attained correspondence value, the most likely signal match may be identified. Hence a likely set of three pairs of signals is identified, which can then be used to determine a likely collapse state of the whole airway system by comparison with the rows of (an exhaustive version of) Table 1, (or an equivalent such table).

Figure 3:
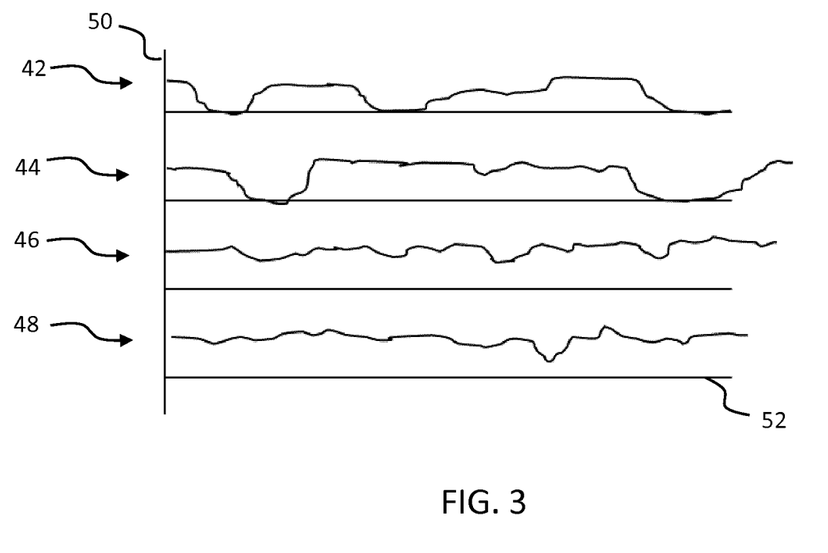
FIG. 3 shows a graph illustrating an example set of acoustic sensor outputs.

An analysis which might be obtained through such 'extent of collapse' methods is illustrated in FIG. 3, in which, in order, the traces 42, 44, 46 and 48 represent an extent of openness (i.e. non-collapse) 50, over time 52, corresponding to the velum, the oropharynx, the tongue and the epiglottis respectively. In the hypothetical case illustrated in FIG. 3, there is significant coexisting collapse at the velum 42 and the oropharynx 44, but no significant collapse at the tongue 46 or epiglottis 48.

The 'audio-catalogue' of baseline signals utilized for these methods may for example be compiled empirically, by fabricating a simulated airway model, establishing artificial 'collapse-like' blockages at each possible combination of V,O,T,E, and recording, using an embodiment of the catheter described above, the sets of signals received.

Alternatively, the catalogue may be compiled through computer (or otherwise analytic) simulation, using a mathematical physical model of the airway and establishing a list of expected signal traces for each (V,O,T,E) configuration at each microphone element.

Note further that for the example catheter of FIG. 1, comprising only three microphone elements and 2 speaker elements, an exhaustive catalogue of possible $S_{\alpha\beta\gamma}$ baseline traces would comprise only 12 entries, the possible signals corresponding to:

$S_{11O}$ $S_{12O}$ $S_{21O}$ $S_{22O}$ $S_{31O}$ $S_{32O}$
$S_{11C}$ $S_{12C}$ $S_{21C}$ $S_{22C}$ $S_{31C}$ $S_{32C}$

Moreover, for each signal received at a given microphone, it is only necessary to compare the signal with four possible reference signals, since the possible signals received at any given microphone is only four (for the particular example of FIG. 1). For other example catheters comprising greater numbers of microphones and speakers, the necessary catalogue would be larger.

Methods described above were described with reference to the particular catheter example depicted in FIG. 1, with the particular arrangement of microphone and speaker elements shown. However, the same methods may applied mutatis mutandis to signals received from catheter embodiments comprising different arrangements of elements, for example comprising a greater number of microphone and/or speaker elements. It will be understood by the skilled person that the concepts of the methods described above are easily transferable, with minor adaptations, to any number of particular catheter arrangements.

Although above methods were described by reference to various one or more graphical mathematical objects, such as Tables and data Catalogues, it is to be understood that these terms are used purely for the purposes of illustration of the concept, and that any particular analytical means may be used to achieve the same end. It is not necessary for instance, that a table, such as Table 1 be used to store entries for reference, as described above, rather some other storage and reference means might be considered instead.

The above described processing and analysis methods may, according to any particular embodiment, be performed by a dedicated processing module comprising processing circuits or processing chips, or might be performed by software on a computer, for example, or might be performed according to a more manual, non-automated method, for example. The 'audio-catalogue' described above may be stored and reference by means of one or more memory modules or units, for example a computer hard drive or solid state storage device.

According to an aspect of the invention, there is provided a system comprising a catheter in accordance with one or more embodiments described above and a processing unit adapted to receive outputs generated by the microphone elements M1, M2, M3 and to determine on the basis of those outputs the presence and location of any obstructions in the upper airway 14. For example, the processing unit might be adapted so as to receive outputs from microphone elements M1, M2, M3 and to apply to these outputs one or more of the processing method embodiments described above. The processing unit might comprise for example a computer running software, or a dedicated unit comprising dedicated processing chips and/or circuits.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A catheter for use in determining the presence and location of obstructions in an upper airway, the catheter comprising:
   two acoustic transducer elements positioned at different points along a length section of the catheter so as to coincide with different points along the length of said upper airway upon insertion therein, each acoustic transducer element adapted to emit an acoustic signal; and
   three acoustic sensor elements positioned at different points along said length section of the catheter, each adapted to detect one or more of said acoustic signals,
   wherein the two acoustic transducer elements and/or the three acoustic sensor elements are arranged such that, upon insertion in said upper airway, the spaces between themthe two acoustic transducer elements and/or the three acoustic sensor elements are positionable to coincide with one or more of: the velum, the oropharynx, the tongue and the epiglottis, and
   wherein the three acoustic sensor elements are separated by, and interleaved with, the two acoustic transducer elements.

2. The catheter as claimed in claim 1, wherein each respective transducer element is adapted to emit an acoustic signal of a different frequency.

3. A system for detecting and determining the location of obstructions within an upper airway and/or oral cavity, the system comprising:
   the catheter as claimed in claim 1; and
   a processing unit adapted to receive one or more outputs generated by each of the acoustic sensor elements, the one or more outputs representative of intensities of each of the acoustic signals detected by respective acoustic sensor elements, and to determine on a basis of said intensities of detected signals, the presence of an obstruction within the upper airway, and a position of said obstruction, relative to the position of one or more of said acoustic sensor elements.

4. The system as claimed in claim 3, wherein the processing unit is adapted to determine the presence and position of said obstruction by comparison of the signal intensities detected at each acoustic sensor element with one or more reference intensities stored in a memory.

5. The system as claimed in claim 3, wherein each acoustic sensor element is adapted to detect a respective acoustic signal emitted by each acoustic transducer element, to thereby generate an output representative of a set of detected signal intensities, and wherein the processing unit is adapted to determine the presence and position of the obstruction by comparison of the set of signal intensities detected at each acoustic sensor element with one or more reference sets stored in a memory.

6. A method for determining the location of one or more obstructions in an upper airway using a catheter comprising: two acoustic transducer elements positioned at different points along a length section of the catheter so as to coincide with different points along the length of said upper airway upon insertion therein, each acoustic transducer element adapted to emit an acoustic signal; and three acoustic sensor elements positioned at different points along said length section of the catheter, each adapted to detect one or more of said acoustic signals, wherein the two acoustic transducer elements and/or the three acoustic sensor elements are arranged such that, upon insertion in an upper airway, the spaces between the two acoustic transducer elements and/or the three acoustic sensor elements are positionable to coincide with one or more of: the velum, the oropharynx, the tongue and the epiglottis, and wherein the three acoustic sensor elements are separated by, and interleaved with, the two acoustic transducer elements, the method comprising:
   inserting the catheter into the upper airway; and
   with a processing unit:
      receiving intensity values corresponding to intensities of one or more of said acoustic signals detected using the three acoustic sensor elements, the one or more of said acoustic signals received at a plurality of detection points located along the length section of said catheter, each of the one or more of said acoustic signals deriving from an acoustic signal emitted at one of a plurality of emission points spaced along the length section of said catheter using the two acoustic transducer elements, wherein one or more of said acoustic signals generated by the two acoustic transducer elements and/or one or more of said acoustic signals received by the three acoustic sensor elements are generated and received at locations such that the spaces between the two acoustic transducer elements and/or the three acoustic sensor elements coincide with one or more of: the velum, the oropharynx, the tongue and the epiglottis; and
      determining on a basis of the detected intensities of one or more of said acoustic signals at each of the plurality of detection points, a presence and position of an obstruction within said upper airway, relative to the position of the plurality of detection points, wherein the plurality of emission points interleave with the plurality of detection points with three detection points separated by two emission points.

7. The method as claimed in claim 6, wherein the presence and position of said obstruction is determined through comparing the detected intensities at each of the plurality of detection points with one or more reference intensities.

8. The method as claimed in claim 7, wherein each detection point receives a plurality of one or more of said acoustic signals, each acoustic signal of said plurality of one or more of said acoustic signals deriving from one of the plurality of emission points.

9. The method as claimed in claim 8, wherein the determining step comprises grouping the detected intensities according to the detection point of the plurality of detection points at which the corresponding acoustic signal was received, and comparing the hence formed groups of detected intensities against one or more reference groups stored in a memory.

10. The method as claimed in claim 6, wherein each acoustic signal emitted at each emission point of the plurality of emission points has a different frequency.

\* \* \* \* \*